United States Patent
Hacker

(10) Patent No.: US 8,433,117 B2
(45) Date of Patent: Apr. 30, 2013

(54) COMPUTER CONTROLLED SYSTEM FOR LASER ENERGY DELIVERY TO THE RETINA

(75) Inventor: Henry Hacker, McGregor, TX (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 171 days.

(21) Appl. No.: 13/130,380

(22) PCT Filed: Nov. 21, 2009

(86) PCT No.: PCT/US2009/065421
§ 371 (c)(1),
(2), (4) Date: May 20, 2011

(87) PCT Pub. No.: WO2010/059997
PCT Pub. Date: May 27, 2010

(65) Prior Publication Data
US 2011/0222731 A1    Sep. 15, 2011

Related U.S. Application Data

(60) Provisional application No. 61/116,931, filed on Nov. 21, 2008.

(51) Int. Cl.
*G06K 9/00* (2006.01)

(52) U.S. Cl.
USPC ....... 382/128; 250/559.13; 600/318; 604/294

(58) Field of Classification Search .................. 382/100, 382/128, 130, 117; 250/559.13; 600/318, 600/356, 383; 604/294
See application file for complete search history.

(56) References Cited

U.S. PATENT DOCUMENTS 5,029,220 A * 7/1991 Juday ............................. 382/128
5,106,184 A   4/1992 Milbocker
(Continued)

FOREIGN PATENT DOCUMENTS
WO    2005079919 A1    9/2005

OTHER PUBLICATIONS

Patnaik, Bijayananda, "Photocoagulation in the Management of Choroidal Neovascular Membrane", Bombay Hostial Journal, Issue Special, pp. 1-4, printed on Oct. 17, 2008 from http://www.bhj.org/journal/2002_4403_jul/md_354.htm.

(Continued)

*Primary Examiner* — Anand Bhatnagar
(74) *Attorney, Agent, or Firm* — Elizabeth Arwine

(57) ABSTRACT

An embodiment of the invention provides a method that captures a diagnostic image of a retina having at least one lesion, wherein the lesion includes a plurality of spots to be treated. Information is received from a user interface, wherein the information includes a duration, intensity, and/or wavelength of treatment for each of the spots. A real-time image of the retina is captured; and, a composite image is created by linking the diagnostic image to the real-time image. At least one updated real-time image of the retina is obtained using eye tracking and/or image stabilization; and, an annotated image is created by modifying the composite image based on the updated real-time image. A localized laser beam is delivered to each of the spots according to the information, the composite image, and the annotated image.

25 Claims, 6 Drawing Sheets

U.S. PATENT DOCUMENTS

| | | |
|---|---|---|
| 5,767,941 A | 6/1998 | Ferguson |
| 5,943,115 A | 8/1999 | Ferguson |
| 6,325,512 B1 | 12/2001 | Wei |
| 6,758,564 B2 | 7/2004 | Ferguson |
| 6,789,900 B2 * | 9/2004 | Van de Velde ............... 351/221 |
| 6,810,140 B2 * | 10/2004 | Yang et al. ................... 382/154 |
| 7,168,806 B2 | 1/2007 | Abe |
| 7,474,775 B2 * | 1/2009 | Abramoff et al. ............. 382/128 |
| 7,593,559 B2 * | 9/2009 | Toth et al. .................... 382/128 |
| 8,205,991 B2 * | 6/2012 | Wei et al. ...................... 351/246 |
| 2002/0025298 A1 | 2/2002 | Blumenkranz et al. |
| 2002/0054697 A1 * | 5/2002 | Wang ............................ 382/128 |
| 2003/0009155 A1 | 1/2003 | Pawlowski et al. |
| 2003/0174281 A1 | 9/2003 | Herekar et al. |
| 2005/0237486 A1 | 10/2005 | Su et al. |
| 2005/0254008 A1 | 11/2005 | Ferguson et al. |
| 2006/0100677 A1 | 5/2006 | Blumenkranz et al. |
| 2011/0026789 A1 * | 2/2011 | Hsu et al. ..................... 382/128 |

OTHER PUBLICATIONS

Patnaik, Bijayananda, "Photocoagulation in the Management of Choroidal Neovascular Membrane," http://www.bhj.org/journal/2002_4403_jul/md_354.htm, printed on Oct. 17, 2008.

Stuck, Bruce E., "Accidental Human Laser Retinal Injuries from Military Laser Systems," Proceedings of Laser-Inflicted Eye Injuries: Epidemiology, Prevention, and Treatment, SPIE—The International Society for Optical Engineering, Jan. 29-30, 1996, pp. 7-20, vol. 2674.

Zwick, Harry, et al., "Accidental Bilateral Q-Switched Neodymium Laser Exposure: Treatment and Recovery of Visual Function," Proceedings of Laser-Tissue Interaction IX, Jan. 26-28, 1998, pp. 80-89, vol. 3254.

* cited by examiner

COMPUTER CONTROLLED SYSTEM FOR LASER ENERGY DELIVERY TO THE RETINA

I. PRIORITY CLAIM

This application claims the benefit of U.S. Provisional Application Ser. No. 61/116,931 filed on Nov. 21, 2008.

II. FIELD OF THE INVENTION

The present invention is in the field of computer controlled systems for laser energy delivery to the retina.

III. BACKGROUND OF THE INVENTION

Laser retinal injury hazards are present in a variety of military settings. Incident reports abound from adversarial cockpit illumination to battlefield laser rangefinders and target designators as well as episodes of laser injury in government laboratories involved with high energy physics research or other scientific pursuits. Stuck, B. E., H. Zwick, J. Molchany, D. Lund, D. A. Gagliano, "Accidental human laser retinal injuries from military laser," SPIE 2674(7), pp. 7-20 (1996); Zwick H, B. E. Stuck, W. Dunlap, D. K. Scales, D. J. Lund, J. W. Ness, "Accidental bilateral Q-switched neodymium laser exposure: Treatment and recovery of visual function," SPIE 3254, pp. 80-89 (1998). The development of subretinal neovascular membranes represents one of the most vision threatening complications of laser injury.

Currently, treatment of neovascular membranes involves patient rotation through separate stations in order to first diagnose then perform therapeutic membrane ablation using photodynamic therapy (PDT). Treatment involves a cut and paste methodology, with eye care providers estimating lesion size from images generated by the initial patient evaluation. Therapy then occurs with a separate instrument in the general vicinity of suspected retinal involvement. This frequently leads to missing portions of the neovascular membrane resulting in further vision loss and the need for repeat treatments. Thus, current schemes for application of light to produce dye-activation often result in under-treatment and recurrence of the underlying neovascular membrane.

IV. SUMMARY OF THE INVENTION

An embodiment of the invention provides a computer controlled system for laser energy delivery to the retina. More specifically, a method according to an embodiment of the invention captures a diagnostic image of a retina having at least one lesion, wherein the lesion includes a plurality of spots to be treated. Information is received from a user interface, wherein the information includes a duration, intensity, and/or wavelength of treatment for each of the spots. The position and/or size of the spots are determined automatically using an indicator dye locator and/or manually using the user interface. A real-time image of the retina is captured using eye tracking and/or image stabilization techniques. A composite image is created by linking the diagnostic image to the real-time image. At least one updated real-time image of the retina is obtained using eye tracking and/or image stabilization software; and, an annotated image is created by modifying the composite image based on the updated real-time image. A localized laser beam is delivered to each of the spots according to the information, the composite image, and the annotated image.

A device according to an embodiment of the invention includes a retinal imager for capturing a diagnostic image of a retina having at least one lesion, wherein the lesion includes a plurality of spots to be treated. The retinal imager also captures a real-time image and updated real-time images of the retina using eye tracking and/or image stabilization. In at least one embodiment, the indicator dye locator determines the position and/or size of each of the spots. A user interface is provided for receiving information. The information includes a duration, intensity, and/or wavelength of treatment for each of the spots. In at least one embodiment, the information includes the position and/or size of each of the spots. The device further includes a processor for creating a composite image by linking the diagnostic image to the real-time image. The processor also creates an annotated image by modifying the composite image based on the updated real-time image. A laser is provided for delivering a localized laser beam to each of the spots according to the information, the composite image, and the annotated image.

V. BRIEF DESCRIPTION OF THE DRAWINGS

The present invention is described with reference to the accompanying drawings. In the drawings, like reference numbers indicate identical or functionally similar elements.

VI. DETAILED DESCRIPTION OF THE DRAWINGS

Figure 1:
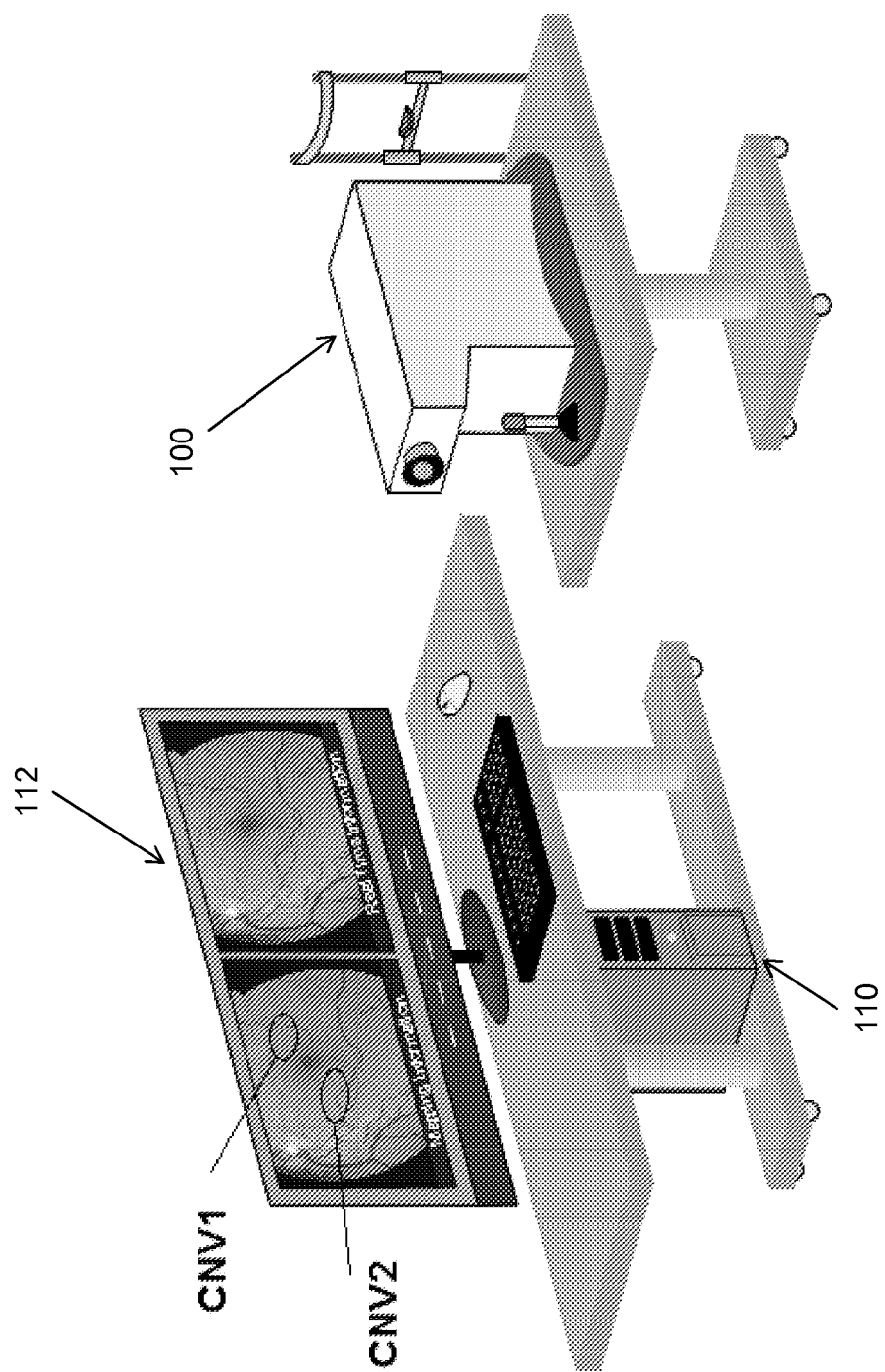
FIG. 1 illustrates a combination SLO/PDT (scanning laser ophthalmoscope/photodynamic therapy) laser therapy instrument.

Exemplary, non-limiting, embodiments of the present invention are discussed in detail below. While specific configurations are discussed to provide a clear understanding, it should be understood that the disclosed configurations are provided for illustration purposes only. A person of ordinary skill in the art will recognize that other configurations may be used without departing from the spirit and scope of the invention.

With high performance digital video technology it is possible to diagnose and identify abnormal neovascular membranes in real-time, capture the precise location of the affected retinal tissue, and utilize the same optical pathway to precisely apply therapeutic photodynamic therapy. An advanced optoelectronic device is provided that allows for the precise application of photodynamic therapy. The basic science behind photodynamic therapy utilizes light to activate a photosensitizing parenterally administered dye that interacts with abnormal blood vessels through the formation and release of oxidizing free radicals. As a consequence of this reaction, neovascular membranes are shut down. This reduces the extension of the original laser eye injury into surrounding unaffected retinal tissue. Clinical application of this device also extends to uncommon wartime cases of punctate inner choroidopathy (PIC) associated with ocular histoplasmosis syndrome, as well as conventional clinical treatment of age-related macular degeneration. From a basic research standpoint, one can compare the efficacy of hand delivery of light for dye activation to computer-assisted delivery of this therapy to improve treatment efficacy and visual outcomes.

An embodiment of the invention provides a device (also referred to herein as the "system") having an interface with an existing scanning laser ophthalmoscope (also referred to herein as a "retinal imager") to process and capture images of retinal neovascular membranes. The device allows for shuttering-in of phototherapeutic laser energy to the affected tissue in real-time. A user can define parameters for a specific therapeutic laser window size, intensity, and/or wavelength. The device may be broadly applied to treatment of neovascular membranes that arise in the retina from a variety of other common medical conditions. For example, ocular histoplasmosis, retinal trauma, diabetic retinopathy, and age related macular degeneration may result in the formation of subretinal neovascular membranes.

The device uses advanced imaging modalities (optical coherence tomography (OCT) and in some embodiments wavefront corrected retinal imaging) to diagnose abnormalities, localizes neovascularization, and provides automated treatment with PDT. The device assesses and treats choroidal neovascularization (CNV) from other causes (e.g., "wet" age related macular degeneration). The device in at least one embodiment manages laser-induced eye injuries and enhances ophthalmological diagnosis and treatment of other maladies at medical centers. Ophthalmic imaging and an in-line PDT laser delivery system are integrated into a single device.

FIG. 1 illustrates a combination SLO/PDT (scanning laser ophthalmoscope/photodynamic therapy) laser therapy instrument 100. Diagnostic images are captured utilizing conventional fluorescein and indocyanine green dyes. These dyes may be administered simultaneously to reduce image capture time and avoid an additional needle stick for the patient. Image capture is performed by the instrument 100 (SLO) with excitation and detection wavelengths appropriate for the fluorescein and/or indocyanine green dyes. The captured images are stored on a computer 110 for real-time review by the treating physician.

As described below, in at least one embodiment, a processor 630 is located in the computer 110; and, a retinal imager 610 and laser 640 are located in the instrument 100. Input from the instrument 100 is received in the computer 110; and, output from the computer 110 is sent to the instrument 100. Treatment images are selected on a display 112 by the medical professional and/or the system and digitally registered to the exact lesion on the stored image (CNV1 and CNV2). These lesions may include leaking microaneurysms, retinal pigment epithelial window defects, neoplasms such as capillary hemangiomas, or other tumors with the eye. If multiple treatment areas are required, each location is programmed for a specific energy level, exposure time, and treatment wavelength (in the case of a tunable treatment laser delivery system). For example, Table 1 illustrates a treatment plan for use with the instrument 100 for the lesions illustrated on the display 112.

TABLE 1

| LESION ID | Spot size | Treatment duration | energy | wavelength |
|---|---|---|---|---|
| CNV 1 | 500 micron | 80 sec | 300 mJ | 680 nM |
| CNV 2 | 2500 micron | 92 sec | 400 mJ | 540 nM |

With the patient positioned at the diagnostic and therapeutic instrument 100, registration of the live (real-time) retinal image is obtained and correlated with the stored image data using image tracking and stabilization software. The correlation in at least one embodiment is based on matching landmarks present in the real-time and stored images. Once lock-on is achieved, the physician may initiate treatment by activation of a footpedal, joystick, or other control mechanism. Each lesion will be treated according to a preprogrammed sequence, e.g., each location is programmed for a specific energy level, exposure time, and treatment wavelength as provided for in the treatment plan. Treatment may proceed smoothly from lesion to lesion as long as the control mechanism is activated. Alternatively, treatment may be activated with audio prompting from the computer 110 in stepwise fashion. The physician may interrupt or resume treatment at any time during the therapeutic laser application. In addition, the control mechanism may be programmed to permit shifting treatment to the next or prior lesion in the programmed sequence. At the conclusion of the treatment session, another series of retinal images may be captured as necessary with or without dye enhancement.

Figure 2:
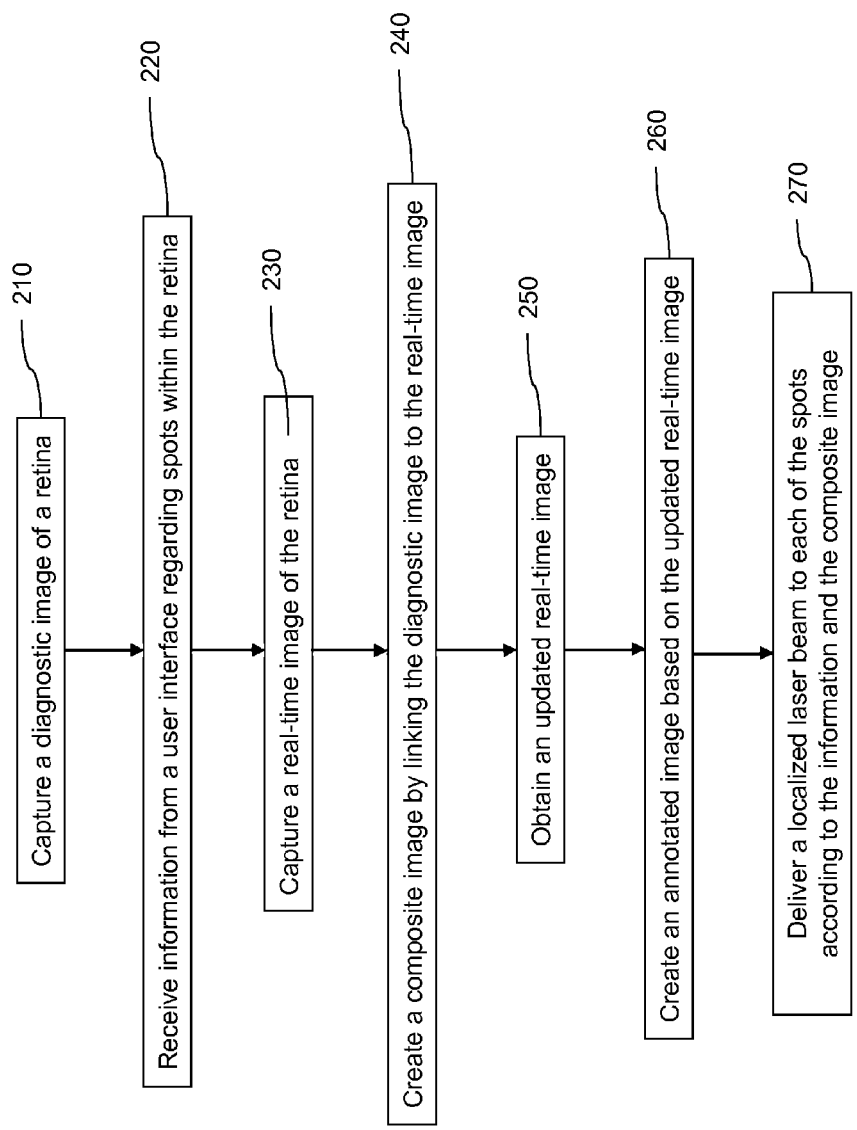
FIG. 2 illustrates a flow diagram illustrating operation of a computer controlled system for laser energy delivery to the retina.

FIG. 2 illustrates a flow diagram of a method according to an embodiment of the invention. A diagnostic image of a retina having at least one lesion is captured, where the lesion includes a plurality of spots to be treated (210). As described above, diagnostic images are captured utilizing conventional fluorescein and indocyanine green dyes. These dyes may be administered simultaneously to reduce image capture time and avoid an additional needle stick for the patient. Image capture is performed by the SLO device with excitation and detection wavelengths appropriate for the fluorescein and indocyanine green dyes.

Information is received from a user interface, wherein the information includes a duration, intensity, and/or wavelength of treatment for each of the spots (220). If multiple treatment areas are required, each location is programmed for a specific energy level, exposure time, and treatment wavelength (in the case of a tunable treatment laser delivery system). For example, Table 1 illustrates a treatment plan for use with the instrument 100. Alternatively, the position and/or size of the spots are determined automatically using an indicator dye locator and/or manually using the user interface. Specifically, the computer 110 includes indicator dye locator software for identifying abnormal vessels on the diagnostic image that are stained by indicator dye. Further, a treatment plan can be mapped out on the diagnostic image using a mouse or other suitable pointing device.

A real-time image of the retina is captured using an eye tracking and/or image stabilization system (230); and, a composite image is created by linking the diagnostic image to the real-time image (240). As described above, the treatment plan that was mapped out on the diagnostic image is linked to an instrument that locks on to the retina using eye tracking and image stabilization so that the real-time view is aligned to the previously registered diagnostic image and treatment plan.

At least one updated real-time image of the retina is obtained using eye tracking and/or image stabilization (250). As described below, an annotated image is created by modifying the composite image based on the updated real-time image (260).

A localized laser beam is delivered to each of the spots according to the information and the composite image (270). The physician may interrupt or resume treatment at any time during therapeutic laser application. In addition, the control mechanism may be programmed to permit shifting treatment to the next or prior lesion in the programmed sequence. At the conclusion of the treatment session, another series of retinal images may be captured as necessary with or without dye enhancement.

Figure 3:
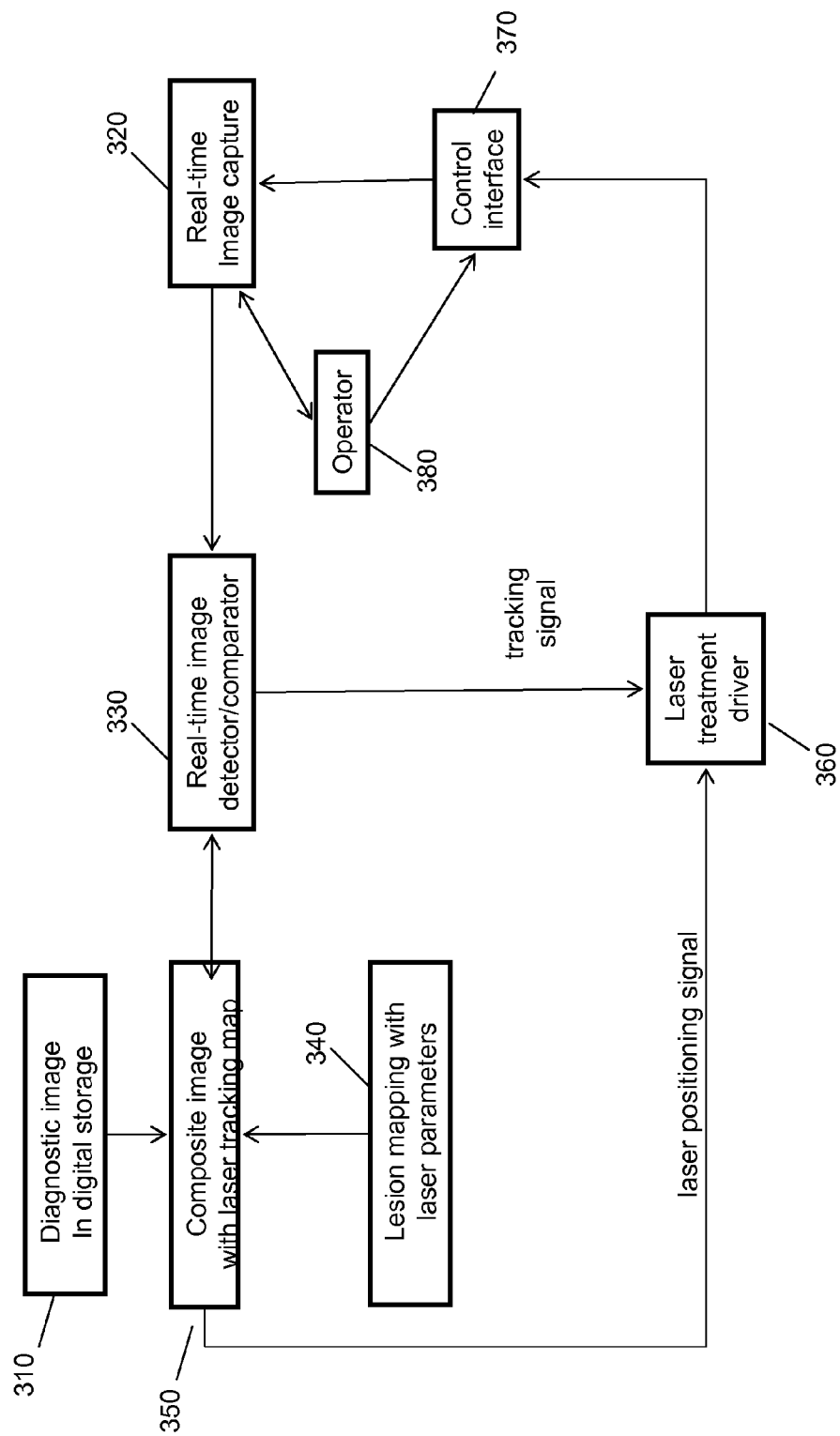
FIG. 3 illustrates an example of focal laser treatment.

FIG. 3 is a flow diagram illustrating operation of a computer controlled system for laser energy delivery to the retina, wherein a diagnostic image is captured and stored in digital storage (310). As described above, diagnostic images are captured utilizing conventional fluorescein and indocyanine green dyes. Image capture is performed by the SLO device with excitation and detection wavelengths appropriate for the dyes. A real-time image is also captured (320) and sent to a real-time image detector/comparator (330). Lesion mapping with laser parameters is performed (340). Specifically, the user can specify laser parameters, such as position and size of spots to be treated on the retina, and duration, intensity, and wavelength of laser treatment. A composite image with a laser tracking map is created (350) using the stored diagnostic image, the image from the real-time image detector/comparator, and the lesion mapping performed in 340. The composite image remains static and does not change throughout diagnosis and laser delivery. As described below, updated real-time images are captured and compared to the composite image to detect eye movement.

The composite image is sent to the real-time image detector/comparator, wherein the composite image is compared to updated real-time images of the retina. A tracking signal is sent to a laser treatment driver from the real-time image detector/comparator (360). The laser treatment driver is used by the system to administer PDT to the retina. The laser treatment driver also obtains a laser positioning signal from the composite image. As described above, an annotated image is created by modifying the composite image so that laser treatment is delivered according to parameters as shown on the annotated composite image.

A control interface is used to capture the real-time images (370). The control interface receives input from the operator of the device (380) and the laser treatment driver. With the patient positioned at the diagnostic and therapeutic SLO 100, registration of the live (real-time) retinal image is obtained and correlated with the stored image data using image tracking and stabilization software. Once lock-on is achieved, the physician may initiate treatment by activation of the control mechanism.

Figure 4:
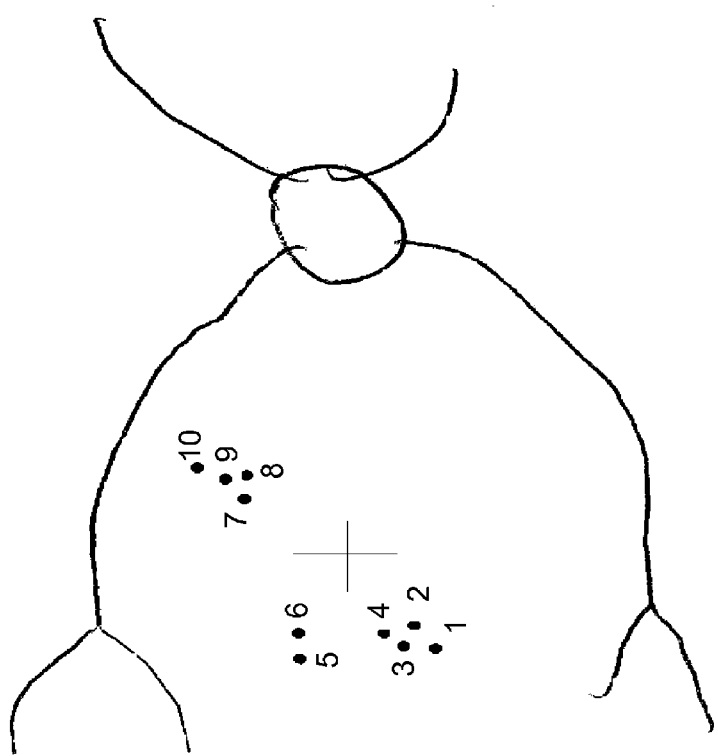
FIG. 4 illustrates an example of scatter laser sector treatment.

FIG. 4 illustrates another example of focal laser treatment. Each spot 1-10 is planned on the diagnostic image. Treatment parameters are shown in the Table 2.

TABLE 2

| Laser treatment ID | Spot size | Treatment duration | Energy | Wavelength |
| --- | --- | --- | --- | --- |
| Spot 1 | 100 micron | 100 millisec | 200 milliwatts | 510 nM |
| Spot 2 | 100 micron | 100 millisec | 200 milliwatts | 510 nM |
| Spot 3 | 100 micron | 100 millisec | 200 milliwatts | 510 nM |
| Spot 4 | 100 micron | 100 millisec | 200 milliwatts | 510 nM |
| Spot 5 | 100 micron | 100 millisec | 200 milliwatts | 510 nM |
| Spot 6 | 100 micron | 100 millisec | 200 milliwatts | 510 nM |
| Spot 7 | 100 micron | 100 millisec | 200 milliwatts | 510 nM |
| Spot 8 | 100 micron | 100 millisec | 200 milliwatts | 510 nM |
| Spot 9 | 100 micron | 100 millisec | 200 milliwatts | 510 nM |
| Spot 10 | 100 micron | 100 millisec | 200 milliwatts | 510 nM |

Figure 5:
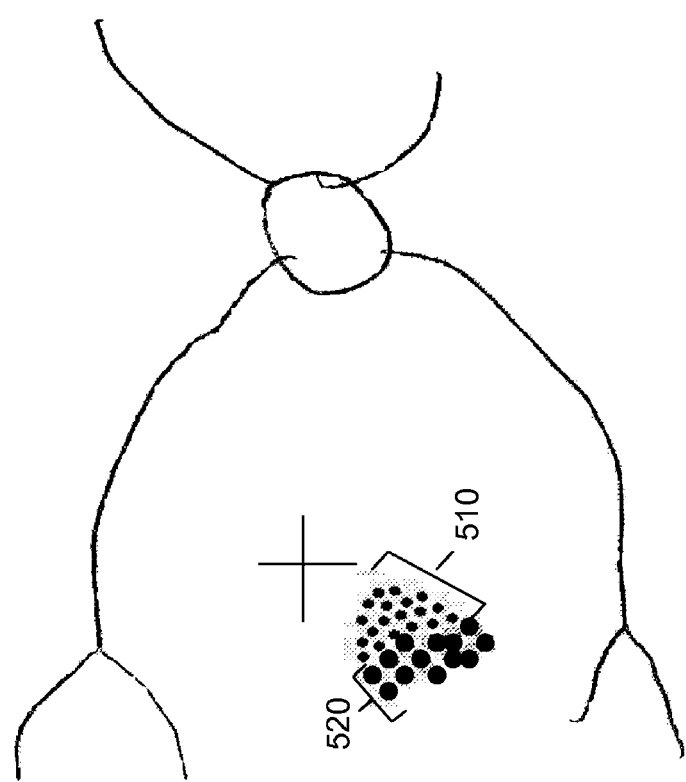
FIG. 5 is a flow diagram illustrating a method according to an embodiment of the invention.

FIG. 5 illustrates an example of scatter laser sector treatment. Each spot is identified on the diagnostic image. Treatment parameters for blue spot group 510 (smaller spots in upper right of cluster) and green spot group 520 (larger spots on left side of cluster) are shown in Table 3.

TABLE 3

| Laser treatment ID | Spot size | Treatment duration | Energy | Wavelength |
| --- | --- | --- | --- | --- |
| Blue spot group | 100 micron | 100 millisec | 200 milliwatts | 510 nM |
| Green spot group | 200 micron | 100 millisec | 300 milliwatts | 510 nM |

In another embodiment of the invention, the device is employed for computer assisted delivery of laser treatment for PDT. The use of PDT involves light activation of a photosensitizing dye that on laser exposure promotes the release of charged molecules that cause blood flow to stop in abnormal vascular beds (neovascular membranes). A treatment plan is mapped out on a diagnostic image using a mouse or other suitable pointing device. This map is then linked to an instrument that locks on to the retina using eye tracking and image stabilization so that the real-time view is aligned to the previously registered diagnostic image and treatment plan. Many of the details of eye tracking are well-known and are not discussed herein in detail so as to focus the reader on the salient portions of the invention. Instead, reference is made to U.S. Pat. No. 5,106,184 to Milbocker and U.S. Pat. No. 6,325,512 to Wei for the description of such details.

The Milbocker patent features a retinal blood flow velocimeter that projects an illumination beam through a steering system onto a retinal vessel, and forms a separate tracking image back through the steering system. A fast tracking loop detects motion of the tracking image and moves the steering system to null image motion and keep the illumination beam centered on the vessel. The beam is reflected from the vessel, picked up by detectors at two fixed angles, and processed by spectral analysis. In one embodiment the illumination beam and the steering system follow entirely separate paths through the steering system. Fiber optics translate the collected Doppler light without dispersion while preserving phase relationships, and absolute dimensions are determined from the image tracking electronics. A processor then computes volumetric blood flow which it compares with normative data.

The Wei patent features an optical coherence tomography ("OCT") application apparatus that performs an OCT application on an object. The OCT application apparatus includes an OCT scanning apparatus which outputs a beam of OCT scanning radiation and an active tracking system that generates and projects a beam of tracking radiation onto a region including a reference tracking feature, which active tracking system includes a tracking optical system that is disposed to intercept the beam of tracking radiation and the beam of OCT scanning radiation. The active tracking system of Wei analyzes tracking radiation reflected from the region to detect movement of the object, and to generate a tracking signal which directs the tracking optical system to follow the movement of the object. In one embodiment of Wei, the OCT application comprises forming an OCT scan image of the object, for example and without limitation, a retina of an eye.

Once positive lock-on is achieved with the registered image, the physician (laser-operator) may initiate treatment. The application of treatment laser energy may be interrupted by the operator at will or by the instrument in the event of loss of eye tracking or loss of correspondence with the registered image (i.e., diagnostic image). Completion of treatment is resumed when the operator and/or instrument have realigned the patient. The instrument retains a record of how much treatment has been applied to specific retinal locations to facilitate accurate resumption of therapy. The computer guided application of light may be extended to the activation of retinal drugs delivered in an encapsulate such as a liposome or employment of other molecules which are light activated that have a therapeutic effect within the area of interest of laser illuminated tissue.

The device allows for rapid and precise placement of PDT. High performance digital image processing and tracking coupled with computer controlled delivery of laser treatment is provided. The use of treatment mapping on digital imagery allows for precise localization of treatment application to a specific area of the retina. An embodiment of the invention uses computer guidance for the precise application of laser delivery to the retina in which the position, energy level, and duration of laser treatment are controlled spot by spot rather than a non-specific uniform energy level grid pattern. The delivery of laser energy may also be performed in a continuous raster application, again with beam intensity and dwell time modified as necessary at any given place in the raster epoch.

Figure 6:
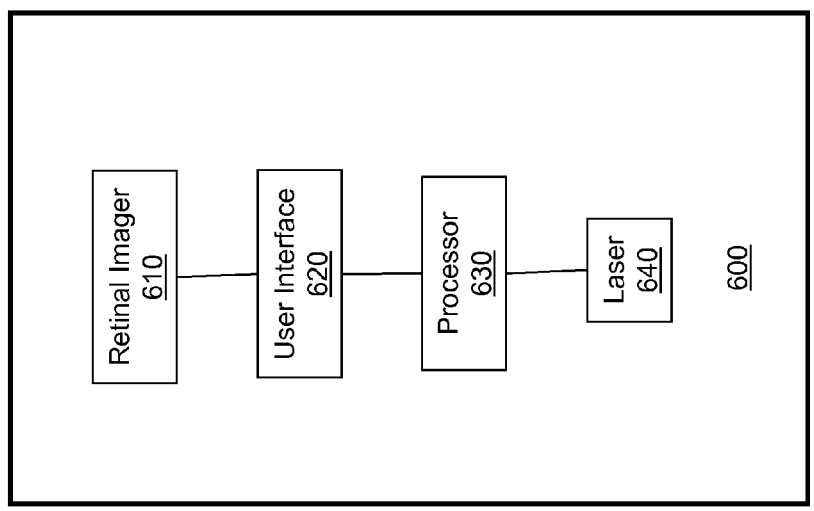
FIG. 6 is a schematic diagram illustrating a device according to an embodiment of the invention.

FIG. 6 is a schematic diagram illustrating a system 600 according to an embodiment of the invention. The system 600 includes a retinal imager 610 for capturing a diagnostic image of a retina having at least one lesion, wherein the lesion includes a plurality of spots to be treated. The retinal imager 610 also captures a real-time image and updated real-time images of the retina using eye tracking and/or image stabilization. In at least one embodiment, the eye tracking determines the position and/or size of each of the spots. With the patient positioned at the diagnostic and therapeutic SLO, registration of the live (real-time) retinal image is obtained with the stored image data using image tracking and stabilization.

A user interface 620 is provided for receiving information. The information includes a duration, intensity, and/or wavelength of treatment for each of the spots. In at least one embodiment, the information includes the position and/or size of each of the spots. As described above, computer guidance is used for the precise application of laser delivery to the retina in which the position, energy level, and duration of laser treatment are controlled spot by spot rather than a non-specific uniform energy level grid pattern.

The device further includes a processor 630 for creating a composite image by linking the diagnostic image to the real-time image. As described above, with the patient positioned at the diagnostic and therapeutic SLO, registration of the live (real-time) retinal image is obtained with the stored image data using image tracking and stabilization. The processor 630 also creates an annotated image by modifying the composite image based on the updated real-time image. In at least one embodiment, the processor 630 is located in the computer 110.

A laser 640 is provided for delivering a localized laser beam to each of the spots according to the information, the composite image, and the annotated image. The delivery of laser energy may be performed in a continuous raster application, with beam intensity and dwell time modified as necessary at any given place in the raster epoch. As described above, an indicator dye locator is also provided for determining the position and/or size of the spots. In at least one embodiment, the retinal imager 610 and laser 640 are located in the instrument 100.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the root terms "include" and/or "have", when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means plus function elements in the claims below are intended to include any structure, or material, for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

VII. INDUSTRIAL APPLICABILITY

The invention can be utilized in a variety of settings to provide accurate imaging, diagnosis and treatment of lesions on a retina by accurately delivering laser energy to particular parts of the retina. For example, a physician wishing to image and treat lesions on a patient's retina would benefit by being able to compare a contemporaneous image of the lesions with previously taken images of the patient's retina prior to delivering laser energy. Also the invention can be used to diagnose and identify abnormal neovascular membranes in real-time, capture the precise location of the affected retinal tissue, and utilize the same optical pathway to precisely apply therapeutic photodynamic therapy.

I claim:
1. A method including:
    capturing a diagnostic image of a retina having at least one lesion, said lesion including a plurality of spots to be treated;
    storing said diagnostic image;
    receiving information from a user interface, said information including at least one of:
        a duration of treatment for each of said spots,
        an intensity of treatment for each of said spots, and
        a wavelength of treatment for each of said spots;
    capturing a real-time image of said retina using at least one eye tracking apparatus;
    creating a composite image by linking said diagnostic image to said real-time image;
    storing said composite image;
    obtaining at least one updated real-time image of said retina using said eye tracking apparatus;
    creating an annotated image by modifying said composite image based on said updated real-time image; and
    delivering a localized laser beam to each of said spots according to said information, said composite image, and said annotated image.

2. The method according to claim 1, further comprising stabilizing said captured images of the retina by processing said images with an image stabilization system.

3. The method according to claim 1, further comprising capturing at least one image of the retina after delivery of said localized laser beam to said spots on the retina.

4. The method of claim 3 further comprising linking said at least one image of the retina, captured after delivery of said localized laser beam to said spots on the retina, to said annotated image of the retina.

5. The method of claim 1 further comprising correlating said stored images with said captured real-time images by matching landmarks present in said stored images and said real time images.

6. The method according to claim 1, further comprising determining the position of each said spot of the plurality.

7. The method according to claim 6, further comprising determining the size of each spot of the plurality.

8. The method according to claim 1, further comprising determining the size of each spot of the plurality.

9. The method according to claim 1, further comprising determining the position and size of each said spot of the plurality by scanning said retina.

10. The method according to claim 1, further comprising introducing indicator dye to said retina.

11. The method according to claim 10, further comprising determining the position of each said spot of the plurality by scanning said retina for an indicator dye introduced to said retina.

12. The method according to claim 11, further comprising determining the size of each spot of the plurality by scanning said retina for an indicator dye introduced to said retina.

13. The method according to claim 12, further comprising introducing a photosensitizing dye to said retina.

14. The method according to claim 13, further comprising delivering a localized laser beam to at least one of said plurality of spots on said retina containing said photosensing dye to promote the release of charged molecules to reduce blood flow in abnormal vascular beds.

15. The method according to claim 10, further comprising determining the size of each spot of the plurality by scanning said retina for an indicator dye introduced to said retina.

16. The method according to claim 1, further comprising determining the position and size of each said spot of the plurality by automatically scanning said retina of an indicator dye introduced to said retina.

17. A device including:
a retinal imager for capturing:
a diagnostic image of a retina having at least one lesion, said lesion including a plurality of spots to be treated,
a real-time image of said retina using at least one of eye tracking and image stabilization, and
at least one updated real-time image of said retina using at least one of said eye tracking and said image stabilization;
a user interface for receiving information, said information including at least one of:
a duration of treatment for each of said spots,
an intensity of treatment for each of said spots, and
a wavelength of treatment for each of said spots;
a processor for creating:
a composite image by linking said diagnostic image to said real-time image, and
an annotated image by modifying said composite image based on said updated real-time image; and
a laser for delivering a localized laser beam to each of said spots according to said information, said composite image, and said annotated image.

18. The device according to claim 17, wherein said information includes at least one of a position and a size of each of said spots.

19. The device according to claim 17, further comprising an indicator dye locator for determining at least one of a position and a size of each of said spots.

20. A system for the precise delivery of laser energy to a retina comprising:
a computer processor;
a retinal imager with eye tracking coupled to said computer processor;
a user interface, said user interface coupled to said retinal imager and said computer processor;
a laser coupled to said user interface through said processor;
wherein said retinal imager captures at least one diagnostic image, and at least one real time image of said retina; said computer processor receives said plurality of images, saves said images, correlates said images, and creates at least one annotated image identifying the location and size of at least one spot on the retinal to receive laser treatment; said computer processor displaying said annotated image and receiving instructions for delivery of laser energy to said retina from said user interface;
said laser coupled to said user interface delivering laser energy specified by said processor to a particular location on the retina.

21. The system of claim 20 wherein said retinal imager further comprises imaging stabilization.

22. The system of claim 21 wherein said processor is programmed to perform image stabilization.

23. The system of claim 21 wherein said laser imager is a scanning laser ophthalmoscope.

24. The system of claim 20 wherein said laser is coupled to said user interface through said processor delivers laser energy to a location on the retina specified by the computer processor.

25. The system of claim 24 wherein said laser is coupled to said user interface through said processor and is positioned to deliver laser energy to a location on the retina containing a photosensitizing dye.

* * * * *